(12) United States Patent
Kraus et al.

(10) Patent No.: US 9,211,103 B2
(45) Date of Patent: Dec. 15, 2015

(54) SYSTEMS AND METHODS FOR GENERATING AN OSTEOARTHRITIS PROGRESSION PREDICTOR AND SYSTEMS AND METHODS FOR USING THE PREDICTOR

(75) Inventors: Virginia Byers Kraus, Durham, NC (US); H Cecil Charles, Durham, NC (US); Sheng Chu Wang, Durham, NC (US); Sheng Feng, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/291,919

(22) Filed: Nov. 8, 2011

(65) Prior Publication Data

US 2012/0114211 A1    May 10, 2012

Related U.S. Application Data

(63) Continuation of application No. 13/119,821, filed as application No. PCT/US2009/005195 on Sep. 18, 2009, now abandoned.

(60) Provisional application No. 61/098,551, filed on Sep. 19, 2008.

(51) Int. Cl.
| | | |
|---|---|---|
| *A61B 6/00* | (2006.01) | |
| *G06T 7/00* | (2006.01) | |
| *G06T 7/40* | (2006.01) | |
| *A61B 5/055* | (2006.01) | |

(52) U.S. Cl.
CPC ............... *A61B 6/469* (2013.01); *A61B 6/505* (2013.01); *G06T 7/0012* (2013.01); *G06T 7/406* (2013.01); *A61B 5/055* (2013.01); *G06T 2207/10072* (2013.01); *G06T 2207/10116* (2013.01); *G06T 2207/20104* (2013.01); *G06T 2207/30008* (2013.01)

(58) Field of Classification Search
CPC ........ A61B 5/055; A61B 6/469; A61B 6/505; G06T 7/0012; G06T 7/406; G06T 2207/10072; G06T 2207/10116; G06T 2207/20104; G06T 2207/30008
See application file for complete search history.

(56) References Cited

U.S. PATENT DOCUMENTS

| | | | | |
|---|---|---|---|---|
| 5,859,919 | A | * | 1/1999 | Holland et al. ............... 382/108 |
| 5,931,780 | A | * | 8/1999 | Giger et al. .................... 600/407 |
| 6,690,761 | B2 | * | 2/2004 | Lang et al. ...................... 378/56 |
| 7,386,154 | B2 | * | 6/2008 | Cosmi ........................... 382/128 |
| 7,539,332 | B1 | * | 5/2009 | Al-Dayeh et al. ............. 382/128 |
| 7,660,453 | B2 | * | 2/2010 | Lang .............................. 382/132 |

(Continued)

OTHER PUBLICATIONS

Buckland-Wright, "Subchondral bone changes in hand and knee osteoarthritis detected by radiography", 2004, OsteoArthritis and Cartilage 12, S10-S19.*

(Continued)

*Primary Examiner* — Katrina Fujita
(74) *Attorney, Agent, or Firm* — Andrus Intellectual Property Law, LLP

(57) ABSTRACT

Example systems and methods of generating an indicator of osteoarthritis (OA) progression are described. Fractal dimension curves are generated for horizontal and vertical trabecular components associated with a region of interest of a joint image. A statistical model is used to model shapes of the fractal dimension curves and a predictor of OA progression is calculated based on shape parameters of the statistical model.

22 Claims, 12 Drawing Sheets

(56) References Cited

U.S. PATENT DOCUMENTS

| | | | |
|---|---|---|---|
| 7,664,298 B2* | 2/2010 | Lang et al. | 382/128 |
| 7,769,213 B2* | 8/2010 | Gregory et al. | 382/128 |
| 7,840,247 B2* | 11/2010 | Liew et al. | 600/407 |
| 8,290,564 B2* | 10/2012 | Lang et al. | 600/407 |
| 2004/0242987 A1* | 12/2004 | Liew et al. | 600/407 |
| 2006/0062442 A1* | 3/2006 | Arnaud et al. | 382/128 |
| 2007/0274442 A1* | 11/2007 | Gregory et al. | 378/54 |

OTHER PUBLICATIONS

Duryea et al, "Trainable rule-based algorithm for the measurement of joint space width in digital radiographic images of the knee", 2000, Medical Physics 27, 580-591.*

Gregory et al, "Early Identification of Radiographic Osteoarthritis of the Hip Using an Active Shape Model to Quantify Changes in Bone Morphometric Features", Arthritis & Rheumatism vol. 56, No. 11, Nov. 2007, pp. 3634-3643.*

Kazakia et al., "New imaging technologies in the diagnosis of osteoporosis", Rev Endocr Metab Disord (2006) 7:67-74.*

Messent et al., "Fractal Analysis of Trabecular Bone in Knee Osteoarthritis (OA) is a More Sensitive Marker of Disease Status than Bone Mineral Density (BMD)", Calcif Tissue Int (2005) 76:419-425.*

Messent et al., "Osteophytes, juxta-articular radiolucencies and cancellous bone changes in the proximal tibia of patients with knee osteoarthritis", OsteoArthritis and Cartilage (2007) 15, 179-186.*

Podsiadlo et al, "Differences in trabecular bone texture between knees with and without radiographic osteoarthritis detected by fractal methods", Osteoarthritis and Cartilage (2008) 16, 323-329.*

Pothuaud et al, "Fractal Dimension of Trabecular Bone Projection Texture Is Related to Three-Dimensional Microarchitecture", Journal of Bone and Mineral Research vol. 15, No. 4, 2000, 691-699.*

Yi et al, "Direct measurement of trabecular bone anisotropy using directional fractal dimension and principal axes of inertia", Oral Surg Oral Med Oral Pathol Oral Radiol Endod 2007;104:110-116).*

Amin et al., "The Relationship Between Cartilage Loss on Magnetic Resonance Imaging and Radiographic Progression in Men and Women With Knee Osteoarthritis", 2005, Arthritis & Rheumatism, vol. 52, No. 10, 3152-3159.*

Kalichman et al., "The association between patellar alignment and patellofemoral joint osteoarthritis features—an MRI study", May 2007, Rheumatology 2007;46:1303-1308.*

Kennedy et al., "Modeling early recovery of physical function following hip and knee arthroplasty", 2006, BMC Musculoskeletal Disorders 2006, 7:100.*

Lammentausta et al., "Prediction of mechanical properties of trabecular bone using quantitative MRI", Phys. Med. Biol. 51 (2006) 6187-6198.*

Chappard et al., "Fractal dimension of trabecular bone: comparison of three histomorphometric computed techniques for measuring the architectural two-dimensional complexity", 2001, Journal of Pathology, vol. 195, Iss: 4, 515-521.*

Dougherty et al., "Lacunarity analysis of spatial pattern in CT images of vertebral trabecular bone for assessing osteoporosis", 2002, Medical Engineering & Physics, vol. 24, Iss: 2, 129-138.*

Madzin et al., "Measurement of Trabecular Bone Structure using Fractal Analysis", Jun. 2008, 4th Kuala Lumpur International Conference on Biomedical Engineering 2008 IFMBE Proceedings, vol. 21, 587-590.*

Majumdar et al., "Fractal analysis of radiographs: Assessment of trabecular bone structure and prediction of elastic modulus and strength", 1999, Medical Physics, vol. 26, Iss: 7, 1330-1340.*

Weinstein et al., "Fractal Geometry and Vertebral Compression Fractures", 1994, Journal of bone and Mineral Research, vol. 9, Iss: 11, 1797-1802.*

Communication under Rule 71(3) EPC (Notice of Intent to Grant) dated Jul. 31, 2013 in counterpart EP Application No. 09 814 898.4.

Patent Examination Report No. 1 dated Oct. 23, 2014 in counterpart Australian Application No. 2009292646.

Decision to Grant a European Patent dated Mar. 20, 2014 in counterpart EP Application No. 09814898.4.

* cited by examiner

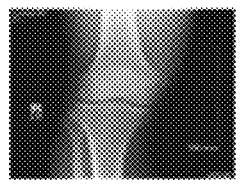 ······ 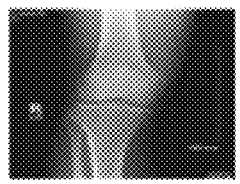
| Radius | FD(V) | FD(H) |
|---|---|---|
| 0.48 | 2.71 | 2.43 |
| 0.64 | 2.57 | 2.36 |
| 0.80 | 2.49 | 2.30 |
| 0.96 | 2.42 | 2.26 |
| 1.12 | 2.36 | 2.30 |
| 1.28 | 2.33 | 2.35 |
| 1.44 | 2.32 | 2.39 |
| 1.60 | 2.40 | 2.49 |
| 1.76 | 2.48 | 2.54 |
| 1.92 | 2.43 | 2.54 |
| 2.08 | 2.36 | 2.54 |
| 2.24 | 2.42 | 2.66 |
| 2.40 | 2.47 | 2.93 |
| 2.56 | 2.32 | 3.08 |
| 2.72 | 2.16 | 2.94 |
······
| Radius | FD(V) | FD(H) |
|---|---|---|
| 0.47 | 2.74 | 2.55 |
| 0.63 | 2.66 | 2.41 |
| 0.78 | 2.55 | 2.44 |
| 0.94 | 2.44 | 2.38 |
| 1.10 | 2.48 | 2.41 |
| 1.25 | 2.57 | 2.45 |
| 1.41 | 2.59 | 2.41 |
| 1.57 | 2.55 | 2.43 |
| 1.73 | 2.46 | 2.40 |
| 1.88 | 2.35 | 2.55 |
| 2.04 | 2.44 | 2.60 |
| 2.20 | 2.55 | 2.71 |
| 2.35 | 2.50 | 2.81 |
| 2.51 | 2.45 | 2.80 |
| 2.67 | 2.45 | 2.85 |
FIGURE 2

| False Positive Rate | Using Covariates | Using FSA |
|---|---|---|
| 0.99 | 1.00 | 1.00 |
| 0.90 | 1.08 | 1.05 |
| 0.80 | 1.23 | 1.07 |
| 0.70 | 1.36 | 1.07 |
| 0.60 | 1.52 | 1.09 |
| 0.50 | 1.68 | 1.13 |
| 0.40 | 1.85 | 1.23 |
| 0.30 | 2.08 | 1.42 |
| 0.20 | 2.73 | 1.78 |
| 0.15 | 3.59 | 2.45 |
| 0.10 | 5.72 | 3.85 |
| 0.09 | 6.72 | 4.17 |
| 0.08 | 8.99 | 4.71 |
| 0.07 | 11.61 | 5.26 |
| 0.06 | 17.33 | 5.85 |
| 0.05 | 23.92 | 7.55 |
| 0.04 | 41.24 | 9.23 |
| 0.03 | 74.75 | 10.91 |
| 0.02 | 398.72 | 12.50 |
| 0.01 | ∞ | 15.00 |

| Factors | Horizontal Fractal Dimension (tension) | | Vertical Fractal Dimension (compression) | |
|---|---|---|---|---|
| | Progression based on OST | Progression based on JSN | Progression based on OST | Progression based on JSN |
| | P values (parameter estimates) | | | |
| radius | < 0.0001 (-0.426) | < 0.0001 (-0.386) | < 0.0001 (0.018) | < 0.0001 (-0.041) |
| radius$^2$ | < 0.0001 (0.202) | < 0.0001 (0.193) | < 0.0001 (0.139) | < 0.0001 (0.134) |
| Left versus Right | 0.732 (0.011) | 0.904 (0.002) | 0.148 (0.038) | 0.108 (0.050) |
| radius*OA_progression | 0.002 (-0.094) | 0.034 (-0.106) | 0.969 (0.001) | 0.895 (0.006) |
| radius$^2$*OA_progression | < 0.0001 (0.036) | 0.023 (0.034) | 0.910 (-0.001) | 0.704 (0.005) |
| Left versus Right*OA_progression | 0.539 (-0.014) | 0.994 (0.0003) | 0.047 (-0.045) | 0.255 (-0.041) |
| Gender | 0.540 (0.009) | 0.5729 (0.008) | < 0.0001 (-0.075) | < 0.0001 (-0.078) |
| Age | 0.323 (-0.0005) | 0.3130 (-0.0006) | 0.008 (0.001) | 0.005 (0.001) |
| BMI | 0.983 (0.00002) | 0.916 (0.0001) | 0.001 (0.003) | 0.0003 (0.003) |
| BMC | 0.0187 (-0.005) | 0.018 (-0.005) | 0.758 (-0.0007) | 0.868 (-0.0004) |
| Knee Pain | 0.873 (-0.001) | 0.885 (-0.001) | 0.004 (0.023) | 0.004 (0.023) |
| Knee Alignment | 0.673 (0.001) | 0.769 (0.0004) | 0.292 (0.001) | 0.206 (0.002) |
| Baseline JSN status | 0.671 (-0.003) | 0.663 (-0.003) | < 0.0001 (0.033) | < 0.0001 (0.033) |

FIGURE 9

| Factors | Outcomes | | | | | |
|---|---|---|---|---|---|---|
| | Any JSN | Medial JSN | Lateral JSN | Any OST | Medial OST | Lateral OST |
| | P values from Type 3 GEE Models (parameter estimates) | | | | | |
| Left vs. right | 0.397 (-0.307) | 0.635 (-0.251) | 0.317 (-0.530) | 0.817 (-0.053) | 0.673 (0.113) | 0.908 (-0.028) |
| Age | 0.384 (-0.020) | 0.025 (-0.088) | 0.032 (0.067) | 0.419 (0.012) | 0.978 (0.001) | 0.719 (0.005) |
| Gender | 0.654 (0.245) | 0.589 (-0.473) | 0.178 (1.019) | 0.605 (-0.174) | 0.554 (-0.239) | 0.934 (-0.030) |
| BMI | 0.352 (-0.042) | 0.067 (-0.115) | 0.503 (0.063) | 0.068 (0.043) | 0.241 (0.027) | 0.036 (0.053) |
| BMC | 0.387 (-0.062) | 0.245 (0.153) | 0.193 (-0.143) | 0.896 (0.007) | 0.988 (0.001) | 0.681 (-0.024) |
| Knee Pain | 0.629 (-0.133) | 0.110 (-0.669) | 0.874 (-0.055) | 0.108 (-0.301) | 0.744 (-0.064) | 0.286 (-0.203) |
| Knee Alignment | 0.119 (-0.113) | 0.016 (-0.252) | 0.610 (-0.057) | 0.096 (0.045) | 0.523 (0.018) | 0.063 (0.060) |
| Baseline JSN Status | 0.120 (-0.377) | 0.494 (-0.201) | 0.167 (-0.533) | 0.026 (0.372) | 0.005 (0.592) | 0.322 (0.171) |
| V_linear (compression) | 0.019 (-9.081) | 0.010 (18.225) | 0.631 (-1.701) | 0.515 (-1.275) | 0.129 (-3.235) | 0.586 (-1.140) |
| V_quad (compression) | 0.025 (-27.531) | 0.015 (58.807) | 0.760 (-3.057) | 0.508 (-3.941) | 0.180 (-8.942) | 0.535 (-3.896) |
| H_linear (tension) | 0.042 (4.585) | 0.012 (10.163) | 0.721 (1.105) | 0.893 (0.210) | 0.191 (2.380) | 0.626 (-0.752) |
| H_quad (tension) | 0.062 (10.926) | 0.021 (24.153) | 0.551 (4.495) | 0.728 (-1.569) | 0.474 (3.895) | 0.371 (-4.133) |

FIGURE 10

| Factors | Time Interval | Horizontal Fractal Dimension (tension) | | Vertical Fractal Dimension (compression) | |
|---|---|---|---|---|---|
| | | Progression based on CA | Progression based on JSN | Progression based on CA | Progression based on JSN |
| | | P values (parameter estimates) | | | |
| Knee OA (n=60) | | | | | |
| radius*OA_progression | 12 months | 0.922 (1.90) | 0.393 (1.16) | 0.045 (-36.35) | 0.329 (-1.22) |
| radius²*OA_progression | | 0.942 (3.94) | 0.388 (3.31) | 0.072 (-108.86) | 0.270 (-4.62) |
| radius*OA_progression | 24 months | 0.698 (6.73) | 0.180 (1.84) | 0.002 (-53.45) | 0.102 (-2.10) |
| radius²*OA_progression | | 0.821 (11.18) | 0.199 (5.03) | 0.002 (-172.02) | 0.043 (-9.67) |
| Non-Knee OA (n=67) | | | | | |
| radius*OA_progression | 12 months | 0.233 (14.53) | 0.233 (14.53) | 0.786 (4.32) | 0.786 (4.32) |
| radius²*OA_progression | | 0.118 (58.95) | 0.118 (58.95) | 0.624 (24.77) | 0.624 (24.77) |
| radius*OA_progression | 24 months | 0.722 (3.73) | 0.722 (3.73) | 0.274 (14.55) | 0.274 (14.55) |
| radius²*OA_progression | | 0.400 (27.30) | 0.400 (27.30) | 0.310 (42.80) | 0.310 (42.80) |

FIGURE 11

| Factors | Timepoint | Horizontal Fractal Dimension (tension) | | Vertical Fractal Dimension (compression) | |
|---|---|---|---|---|---|
| | | Severity based on CA | Severity based on JSN | Severity based on CA | Severity based on JSN |
| | | P values (parameter estimates) | | | |
| Radius | 12 month | 0.0791 (-19.67) | 0.5630 (-0.39) | 0.0043 (-32.78) | 0.1065 (-1.11) |
| radius² | | 0.0895 (-55.91) | 0.6386 (-0.92) | 0.0068 (-98.79) | 0.2322 (-2.61) |
| radius | 24 months | 0.7164 (-3.23) | 0.0637 (1.09) | 0.0006 (-33.67) | 0.0275 (-1.45) |
| radius² | | 0.8518 (-4.89) | 0.0681 (-3.18) | 0.0022 (-94.94) | 0.0786 (-3.67) |

CA=cartilage area; JSN= joint space narrowing

FIGURE 13

SYSTEMS AND METHODS FOR GENERATING AN OSTEOARTHRITIS PROGRESSION PREDICTOR AND SYSTEMS AND METHODS FOR USING THE PREDICTOR

CROSS-REFERENCE TO RELATED APPLICATION

This application is a continuation of U.S. application Ser. No. 13/119,821, filed Mar. 18, 2011, which is the U.S. national phase of International Application No. PCT/US2009/005195, filed Sep. 18, 2009, which designated the U.S. and claims the benefit of U.S. provisional Application No. 61/098,551, filed Sep. 19, 2008, the contents of each of which are incorporated herein in their entirety.

BACKGROUND AND SUMMARY

This patent application describes systems and methods for generating one or more predictors of osteoarthritis (OA) progression. Such predictors can be used, for example, in clinical settings to identify those individuals having an increased risk of OA progression. More specifically, this patent application describes systems and methods which use fractal signature analysis (FSA) to generate such predictors. Example systems and methods for using the predictors are also described herein.

Osteoarthritis (OA) is the leading cause of disability among persons aged 18 years and older. Currently, a total of 40 million Americans (two-thirds of whom are younger than 65), and 450 million individuals worldwide, are affected by arthritis. Direct medical costs are 81 billion dollars in the United States. More than half of all arthritis is due to OA. By the year 2030, the number of people with arthritis is expected to rise to 75 million; the majority of this rise is due to OA, the most common arthritis with aging that is increasing in prevalence due to the aging and increasing obesity of the population.

OA progression can be defined anatomically by means of plain radiographs, clinically by means of symptoms, or physiologically by means of a functional assessment. Of these three methods of defining OA progression, the anatomical means of assessment has prevailed. The only method currently accepted by regulators for evaluating disease progression in knee OA is the sequential radiographic assessment of joint space narrowing (JSN). Problems with radiographic evaluation of OA include difficulty reproducing patient position in order to measure joint space width, and relative insensitivity to change that requires large studies of 18 to 24 months duration to demonstrate changes. Further, changes in joint space width are confounded by meniscal damage and extrusion, which are also seen in OA. Risk factors such as body mass index (BMI), age, and gender are commonly used in OA clinical trials in an attempt to select individuals with greater risk of knee OA progression. However, the effect or interaction of these predictors is not well understood and they have not been highly successful. The continued lack of a good predictor has stalled pursuit of treatments for a disease that affects nearly twenty percent of the population and has a significant impact on productivity and quality of life.

Analyses of bone in OA date back over more than half a century and have provided clear indications that changes in periarticular bone occur very early in OA development. The bone architecture on radiographic images of osteoarthritic joints began to be analyzed in the 1990's by Buckland-Wright and colleagues using fractal signature analysis (FSA), a technique first applied in medicine to the study of abnormalities of lung radiographs. FSA evaluates the complexity of detail of an image (in this case a 2-dimensional image constituting a projection of the 3-D bone architecture) at a variety of scales spanning the typical size range of trabeculae (100-300 micrometers) and trabecular spaces (200-2000 micrometers). As described by Buckland-Wright and colleagues, the complexity of detail quantified by fractal dimension is determined principally by the number, spacing, and cross-connectivity of trabeculae. By nuclear magnetic resonance (NMR), another group has determined that the apparent fractal dimension is an index of bone marrow space pore size; pore size is in turn related to, and increases with, perforation and disappearance of trabeculae.

To date, fractal analysis has been applied successfully to the study of osteoporosis and arthritis of the spine, hips, pre- and post-joint replacement knees, anterior cruciate ligament ruptured knees, wrist, and hands. Plain radiographs have been used primarily, but the fractal analysis method is amenable to use of other image types such as those acquired by computed tomography and NMR.

One advantage of FSA is that it is robust to many of the pitfalls inherent in the gold standard measure of radiographic progression, joint space narrowing. Joint space narrowing is problematic due to the need for high quality images (often beyond the general quality of clinical images) using well-controlled acquisition protocols for extraction of good quantitative data. In particular, FSA has been shown to be robust to varying radiographic exposure, to changing pixel size, and knee repositioning.

To date, three studies have evaluated tibial cancellous bone changes longitudinally in the context of knee OA progression using FSA, but results have been conflicting. The first, a study of 240 patients reported in abstract form only, revealed significant differences in the pattern of FSA change (increased vertical FSA of most trabecular sizes and decreased horizontal FSA of large trabeculae) over 12 months between patients with slow (n=240) versus marked (n=12) joint space narrowing; these results were interpreted as indicative of local subchondral bone loss coincident with knee OA progression. A second much smaller study (n=40) failed to identify significant differences in the pattern of FSA change over the course of 24 months in slow and fast progressors. A third study evaluated FSA change over 3 years in one-third (n=400) of patients in a placebo-controlled trial of a bisphosphonate for knee OA. Compared with patients with non-rapid joint space narrowing (JSN), patients with rapid JSN tended to have a greater decrease in the vertical fractal dimensions (interpreted as a greater loss of most sizes of vertical trabeculae), and no significant difference in the horizontal trabeculae. By contrast, the non-progressor group showed a slight decrease in fractal dimensions for vertical and horizontal trabeculae over time and no drug treatment effect. The JSN progressors showed a marked and dose-dependent change in FSA with drug treatment consistent with a preservation of trabecular structure and reversal of the pathological changes with increasing drug dose.

The example systems and methods described in this patent application employ FSA for predicting OA progressors (e.g., for knees) using a generalized "shape analysis" of data that enables creation of an overall model which is predictive of OA progression independent of other non-radiographic variables.

In fractal signature data, the compression (vertical trabecular) and tension (horizontal trabecular) fractal dimension measures are calculated over a range of radii. The trends of compression and tension change over radius are modeled with polynomial (e.g., second order) multiple regression models. Covariates such as age, gender, BMI may be incorporated as well. The statistical correlations between clinical observations from the same individual are estimated with generalized linear models (GLM) and/or generalized estimation equations (GEE). The estimated regression coefficients are calculated for each individual from the model parameter estimates, and used in a second GLM/GEE model to generate a statistical score representing osteoarthritis progression-risk status.

Receiver operating characteristic (ROC) curves are generated based on the statistical scores using cross-validations. In the cross-validation, data are divided randomly into 5 folds, 4 folds are used to build the model and the remaining 1 fold is used to validate the model parameters.

Using the above-described approach, osteoarthritis progression over time, defined by joint space narrowing (JSN) has been found to be significantly associated with baseline fractal signatures. The regression coefficients estimated from the multiple regressions can predict the OA progression, independent of other covariates (age, gender, body mass index (BMW. This approach can be used, by way of example and without limitation, to power an OA treatment trial using more rapid progressors to thereby decrease the number of trial participants needed to show an effect, which in turn, reduces costs and drug exposure.

BRIEF DESCRIPTION OF THE DRAWINGS

FIG. 1A provides a graphical illustration of the method and FIG. 1B provides a text-based illustration of the method steps.

FIG. 2 shows example radii and corresponding fractal dimension (FD) measures for two separate patients. FD(V) refers to the vertical trabecular dimensions and FD(H) refers to the horizontal trabecular dimensions.

FIG. 9 shows bivariate associations with fractal dimensions in OA progressors and OA non-progressors.

FIG. 10 shows prediction modeling of OA progression defined by joint space narrowing (JSN) or osteophyte (OST).

FIG. 11 shows baseline subchondral medial bone texture (FSA) predicted OA progression in study #2 based on change in cartilage area (CA which is joint space width integrated over the medial compartment) or JSN.

FIG. 13 shows subchondral medial bone texture as an OA severity marker (p values and parameter estimates). Modeled here is change in FSA versus change in cartilage area or change in joint space width (JSN). The data are adjusted for baseline CA or JSW. The only other covariate is site.

DETAILED DESCRIPTION OF EXAMPLE EMBODIMENTS

Figure 1B:
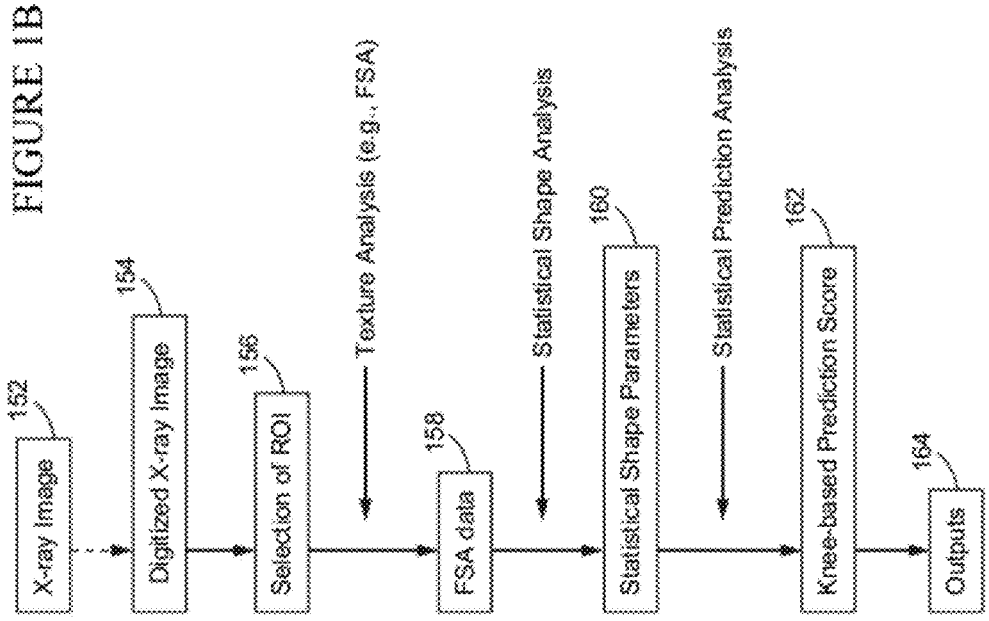
FIGS. 1A and 1B illustrate a non-limiting, example method of generating a predictor of OA progression.

The example systems and methods described herein are based on a recognition that baseline bone texture of the medial tibial plateau is predictive of medial knee joint space narrowing. As described in greater detail below, bone texture reflects the number, spacing, and cross-connectivity of bone trabeculae using fractals. While the traditional covariates (age, gender, body mass index, knee pain), general bone mineral content, and baseline joint space width are little better than random variables for predicting OA progression (52-58% predictive capability), bone texture alone had a 75% predictive capability for knee OA progression at 3 years.

Although trabecular structure is not truly fractal in nature, trabeculae possess fractal-like properties at the resolution of the plain radiograph. For this reason, fractal analysis is a valuable analytic tool for characterizing the complicated histomorphometry of bone. One of the major challenges posed by FSA studies is how to analyze the complex fractal signature data. Prior studies of FSA and OA generally relied on subtraction of the mean fractal signature of an OA or treatment group from that of a non-OA control or reference group.

The example systems and methods described in greater detail below analyze the complex FSA data based on a global curve shape analysis. These systems and methods indicate that changes in periarticular bone are sensitive indicators and likely form part of the disease process in human OA, and provide a prognostic factor with high predictive capability for subsequent cartilage loss.

Currently many computer software programs can process X-ray images of knees and other joints and generate large amounts of information. Knowing how to use such information to enhance the quality of clinical science and clinical practice remains a challenge. Specific clinical questions include: (1) whether some of the bone texture information is useful for predicting OA progression, (2) whether some of the bone texture information is useful as a surrogate measure of OA progression, and (3) how is such information useful. The answer to the first two questions is largely dependant on the technical solution to the third question. Appropriate analytical procedures can be used to link the image information to the clinical outcomes.

The example systems and methods described herein provide such an analytical procedure. They are specifically designed for one type of information, namely fractal dimensions (FD), which can be readily extracted and calculated from images, such as X-rays, computerized tomography, and magnetic resonance images (to name a few), using common imaging processing software. The systems and methods can summarize the FD data and create parameters that are significantly associated with OA progression and can be used to predict OA progression. They can create parameters that correlate with established OA measures of disease severity and that can be used as surrogate measures of OA severity.

The technology described herein was developed using x-ray images from the Prediction of Osteoarthritis Progression (POP) study (Example Study #1 discussed in greater detail below), and validated using x-ray images from an independent OA cohort (Example Study #2 discussed in greater detail below). An analysis of fractal dimension, which reflects the complexity of the bone structure, provides a sensitive means or predicting risk of OA development and progression and can serve as a surrogate marker of disease severity.

Figure 1A:
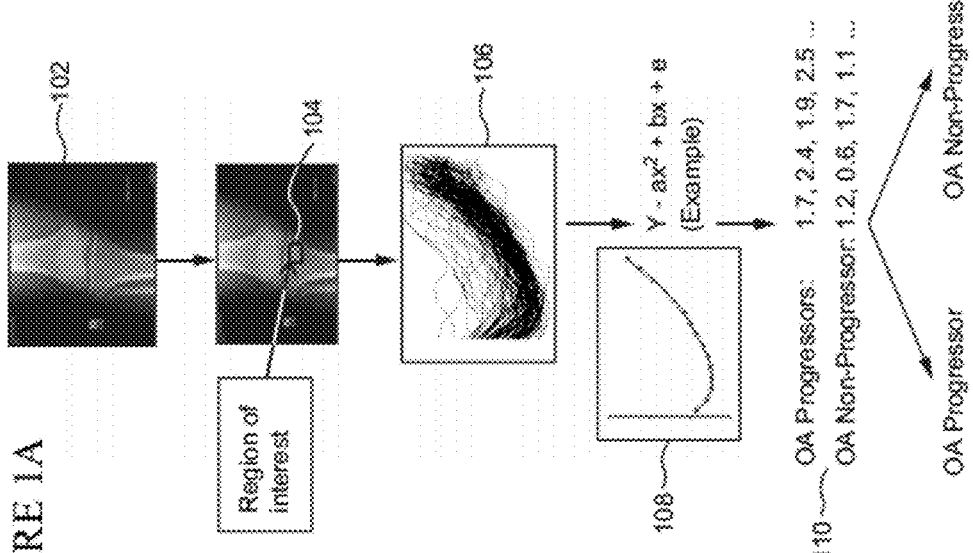

FIGS. 1A and 1B illustrate a non-limiting, example method of generating a predictor of OA progression. FIG. 1A provides a graphical illustration of the method and FIG. 1B provides a text-based illustration of the method steps.

With reference to FIG. 1B, the method starts at 152 with an X-ray image, an example of which is shown at 102 in FIG. 1A. X-ray image 102 is of a knee, but the systems and methods herein may be applied to generating predictors for joints other than knees. X-ray imaging is well-known and is not discussed further herein.

At 154, the X-ray image is digitized. Here again, digitizing of images is well-known and is not discussed further herein.

At 156, a region of interest (ROI) is selected. A region of interest 104 is shown in FIG. 1A and, in this example, spans three-quarters (¾) of the tibial compartment width, has a height of 6 mm and left boundary aligned with the tip of the medial tibial spine. Of course, the ROI for each joint site will need to be determined and optimized and ROI 104 is identified by way of example and without limitation.

Texture analysis is then performed to provide FSA data at 158. Example fractal signature curves are shown at 106 in FIG. 1A.

Statistical shape analysis of the FSA is performed to provide statistical shape parameters at 160. As explained in greater detail below, this analysis involves modeling the shape of each FSA curve. Various statistical methods may be used including, but not limited to, spline, Fourier series, wavelet, polynomial and the like. In one example analysis, second order polynomial regressions are used as generally shown at 108.

The shape parameters are used in statistical prediction analysis to provide a knee-based prediction score at 162 which is output at 164. For example, the shape parameters can be used as predictors in a statistical generalized estimating equation (GEE) model or as predictors in a statistical linear mixed model. Example scores for progressors and non-progressors are shown at 110 in FIG. 1A.

The example method can be viewed as including two major steps. The first step is pre-processing and data generation and the second step is statistical shape analysis and prediction.

The pre-processing and data generation step generates data for follow-up analyses and includes steps 152-158 discussed above. Many computer software packages are available to process (e.g., digitize) X-ray images and generate large amounts of data with all kinds of measures. Consequently, this patent application does not focus in detail on this digitizing. In the example systems and methods described herein, use is made of KneeAnalyzer™ software available from Optasia Medical, Inc. for image processing and fractal dimension (also call fractal signature) data generation from the digitized image data.

While this example uses x-ray images of the knee, the applicability of the method is not limited to knees as noted above. Thus, the method can be applied to x-rays of other joints (e.g., hands, feet, spine, hip, elbow, shoulder, and the like) to provide a predictor of OA progression. Moreover, the images are not limited to x-ray images, but can include other types of images such as computerized tomography, and magnetic resonance images.

Bone texture information is extracted from an image such as a knee x-ray as follows.

Figures 7, 8:
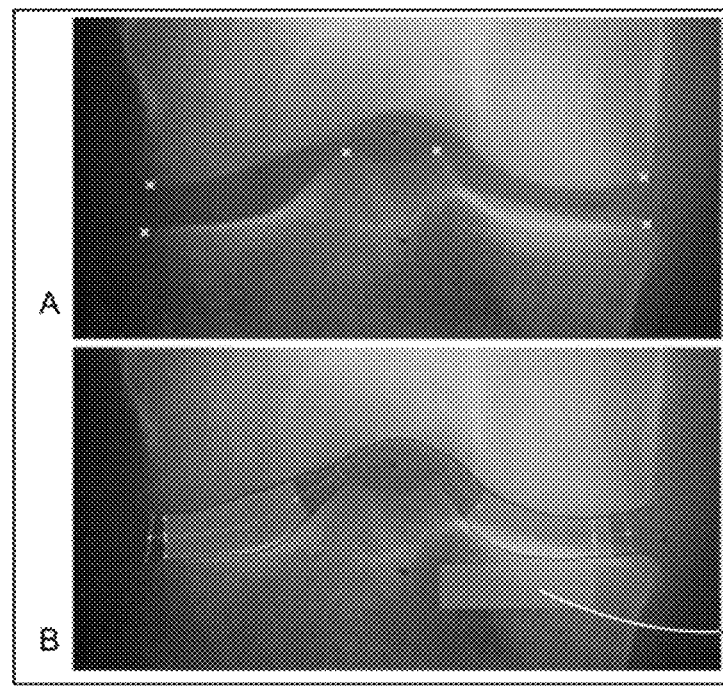
FIG. 7 shows numbers needed to screen to predict one medial joint space narrowing progressor using the traditional approach based on age, gender and body mass index (covariates) or using bone texture analysis (FSA).
FIG. 8 shows an example X-ray.

Choice of Region of Interest (ROI): A ROI is selected for the texture analysis. The ROI is generally selected based on the interests of the investigators. By way of example and without limitation, illustrative ROI 804 (FIG. 8) spans three-quarters (¾) of the tibial compartment width, has a height of 6 mm and left boundary aligned with the tip of the medial tibial spine.

Texture Analysis with FD: FD is a concept of the fractal signature analysis, which is one type of texture analysis. The above-mentioned KneeAnalyzer™ software is used to calculate FD from an ROI. The FD at different scales (radii) generates a 3-dimensional fractal signature. The fractal dimension (FD) is measured in both the horizontal and vertical directions. Representative radii and corresponding FD measures are shown in an example in FIG. 2 for two separate patients.

The statistical shape analysis and prediction step occurs after FD bone texture (fractal signature) data are generated from a ROI of an image and includes steps 160-164 shown in FIG. 1B. The shape of the fractal signature curves is analyzed as described below. Without appropriate statistical modeling, the FD data themselves are hard to use directly to predict OA progressions, even if they contain important and useful information.

The shape of the FD curves for horizontal (FIG. 3A) and vertical (FIG. 3B) trabecular dimensions yield a family of curves that provide information about the vertical (compression component) bone trabeculae (bottom) and the horizontal (tension component) bone trabeculae (top).

Shape Analysis of FD curves: The example systems and methods model the shape of each FSA curve. There are various statistical methods for shape analyses, such as spline, Fourier series, wavelet, polynomial, and the like. In certain example analyses, second order polynomial regressions were used. That is, for each FSA curve generated from image i, $$H_{ij} = a_i x_j^2 + b_i x_j + c_i + e_{ij}$$

$$V_{ij} = r_i x_j^2 + s_i x_j + t_i + e_{ij}$$

where $x_j$ is the readings of radius j, $H_{ij}$ and $V_{ij}$ is the horizontal and vertical fractal dimension measured at radius j, respectively, and $e_{ij}$ are random errors assumed to follow normal distribution. The four shape parameters, $a_i$ and $r_i$ for the quadratic shape, $b_i$ and $s_i$ for the linear shape, are estimated. Each curve i is summarized and represented by these four shape parameters, $a_i$, $r_i$, $b_i$ and $s_i$.

Figure 3A:
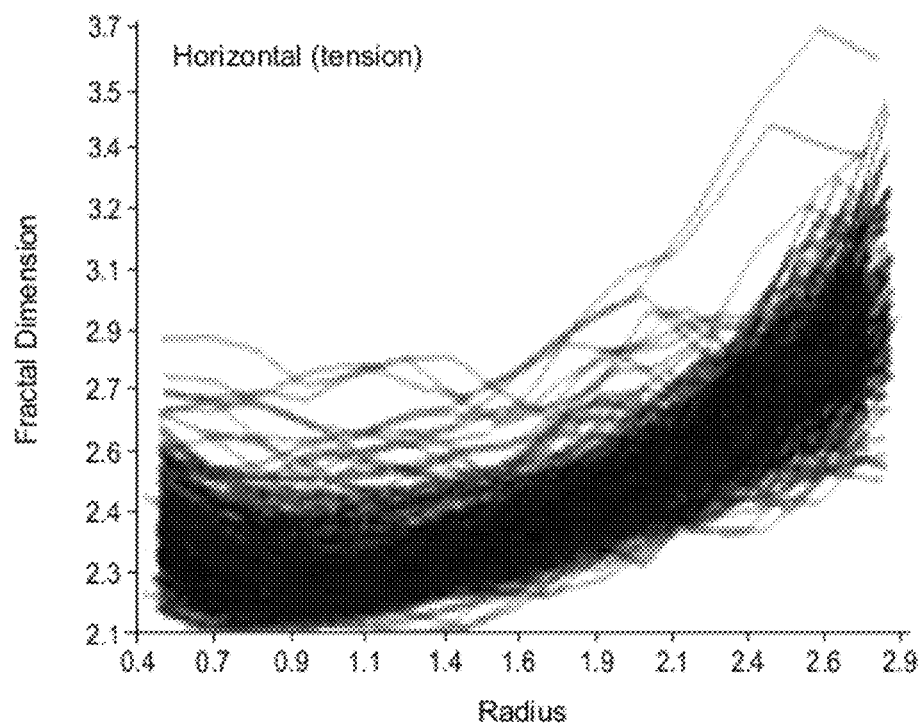
FIGS. 3A and 3B show example FD curves for 138 individuals for the horizontal and vertical trabecular dimensions, respectively.
Figure 3B:
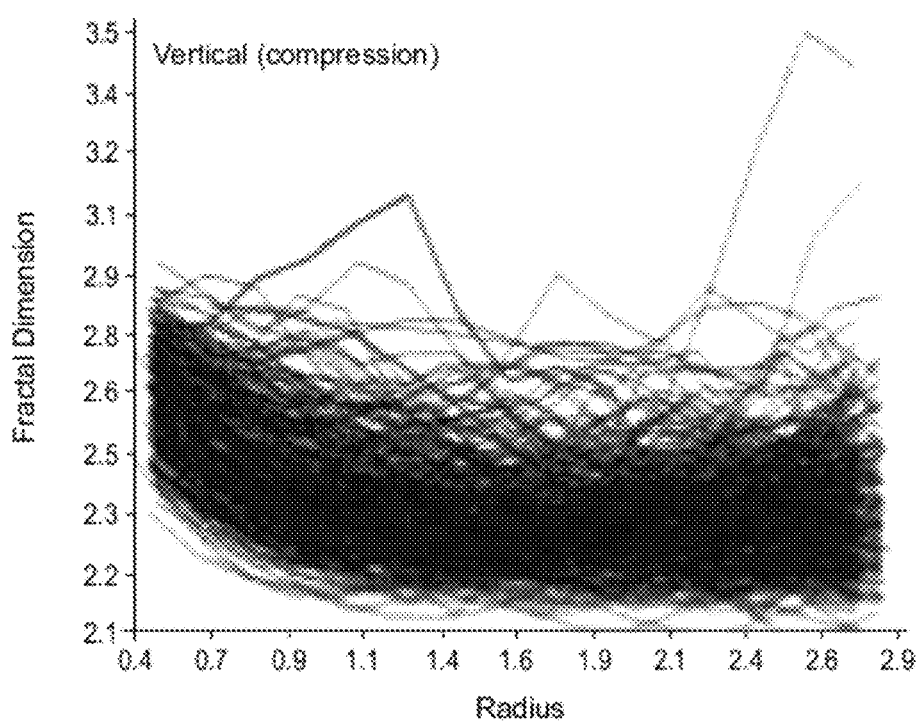

This shape analysis decreases the dimensionality of the data to a manageable and analyzable proportion and also overcomes the complex noise shown by the inter-individual variation in placement of the curve on the y-axis (illustrated in FIGS. 3A and 3B). Once the four shape parameters are obtained, different statistical prediction models can be applied for different experimental designs. Two examples are given below to illustrate how the shape parameters can be used in prediction models.

In a first example data analysis, a statistical generalized estimating equation (GEE) model was chosen to fit the data. The shape parameters were used as predictors in the GEE model. In one instance in which the GEE model was used, the intra-patient variation was non-ignorable, i.e., a large proportion of patients participating in the study had data collected from both knees. All knees were classified as OA progressors or non-progressors in 3 years using a categorical measure (change in categorical JSN). The GEE model is selected because it is designed for this type of experimental design, i.e., the response clinical variable is categorical and there is significant intra-individual variability.

In a second example data analysis, a statistical linear mixed model was chosen to fit the data. The shape parameters were used as predictors in the linear mixed model. In one instance in which the statistical linear mixed model was used, OA patients were selected into the study with age-matched reference population controls. Patients were followed for 2 years, and knee x-rays were obtained at baseline, 12 months and 24 months. The extent of knee OA progression was defined as the change in either of two continuous variables: change in cartilage area measure or JSN (change in continuous minimum joint space width measure). The linear mixed model is selected because it is designed for this type of experiment design, i.e., the response clinical variable can be assumed as a continuous normal variable.

Regardless of which specific model is used, the output of the model is a one-dimensional continuous prediction score for each experimental unit, either a knee or an individual, depending on the experiment design. In the two examples above, the prediction scores were the linear predicted value of the response outcome.

Thus, each individual/knee is assigned a prediction score. The final step is to determine the classification or prediction rule. If a false positive rate is pre-defined, a unique cut-off can be calculated to separate OA progressors from non-progressors. Or, if the false positive rate is not pre-defined, a Receiver Operating Characteristic (ROC) curve can be created with cross-validation procedures.

The method described above may be implemented in hardware, firmware, software and combinations thereof. Software or firmware may be executed by one or more general-purpose or specific-purpose computing devices including a processing system such as a microprocessor and a microcontroller. The software may, for example, be stored on one or more storage media (optical, magnetic, semiconductor or combinations thereof) and loaded into a RAM for execution by the processing system. The software may also be executed from a ROM. Further, a carrier wave may be modulated by a signal representing the corresponding software and an obtained modulated wave may be transmitted, so that an apparatus that receives the modulated wave may demodulate the modulated wave to restore the corresponding program. The systems and methods described herein may also be implemented in part or whole by hardware such as application specific integrated circuits (ASICs), field programmable gate arrays (FPGAs), logic circuits and the like.

Figure 4:
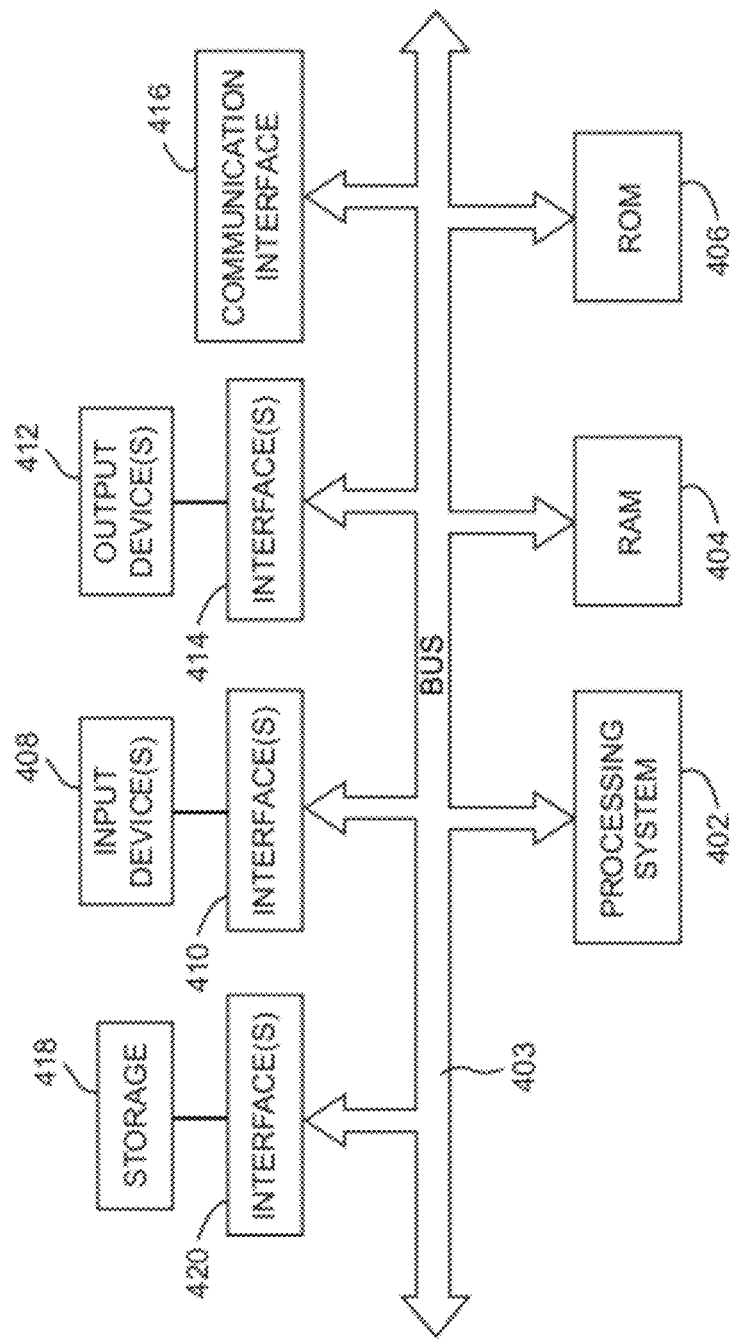
FIG. 4 schematically shows an example computing device.

An example computing device for executing the software or firmware is shown in FIG. 4. The computing device includes a processing system 402 connected by a bus 403 to RAM storage 404, ROM storage 406, input device(s) 408 (through an appropriate interface(s) 410), and output device(s) 412 (through an appropriate interface(s) 414). Typical input devices 408 include, but are not limited to, a keyboard, a pointing device, a microphone, and the like. Typical output devices 410 include, but are not limited to, one or more displays, one or more speakers, one or more printers, and the like. A communication interface 416 allows for wired or wireless communication with other devices, for example, over the interne and/or via the Bluetooth or 802.11 protocols. Other storage device(s) 418 such as a magnetic disk, an optical disk or the like may be connected to the bus via an interface(s) 420. Program code implementing the example method steps described herein may be loaded into RAM storage 404 from storage device(s) 418 and/or ROM 406 for execution by processing system 402. The results of processing such as the FSA curves and the prediction scores may be display on a display or printed by a printer. These results may also be stored in storage device 418. The example computing device may be implemented as a desktop or laptop computer. Of course, the methods described herein can also be implemented as a software addition to existing imaging processing equipment.

Figure 5A:
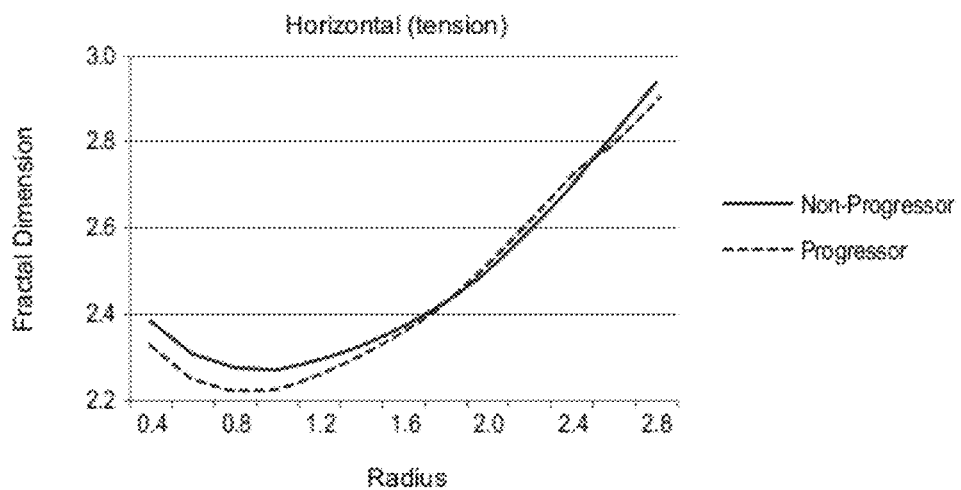
FIGS. 5A and 5B show the mean overall fractal signature shape curves of knee OA progressors and non-progressors for horizontal and vertical trabecular dimensions, respectively.
Figure 5B:
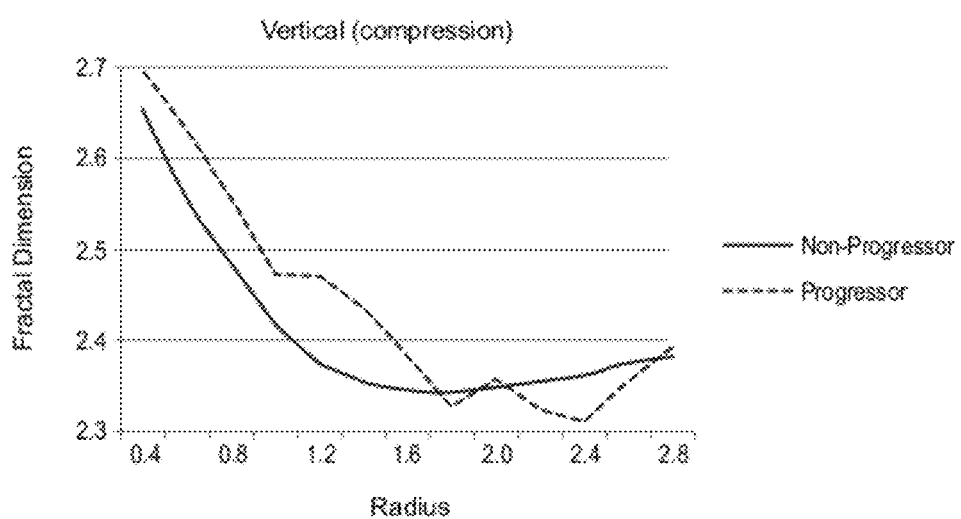

As described above, the example systems and methods involve a strategy that focuses on a global curve fitting approach with a second order polynomial regression. A multi-order ($n^{th}$ order) polynomial is also possible. Using this approach demonstrated that OA progression defined by JSN was significantly associated with shape of the fractal signature curves. Baseline higher fractal signatures of vertical trabeculae and baseline lower fractal signature of horizontal trabeculae distinguished knee OA progressors from non-progressors. FIGS. 5A and 5B shows the mean overall fractal signature shape curves of knee OA progressors and non-progressors for horizontal and vertical trabecular dimensions, respectively.

Age has been associated with increased number (increased FSA) of fine vertical and horizontal trabeculae independent of disease state; in past studies the size of trabeculae affected by age did not overlap the range of trabecular sizes altered by OA. Using the global shape analysis approach, only small effects of age on the vertical FSA were found. Previously, no correlation was found between BMI and FSA. Using the global shape analysis approach, a small but significant effect of BMI on vertical FSA was found.

In summary, OA progression can be predicted based on global shape analysis of fractal signature curves. The prognostic capability of baseline fractal signatures was evaluated to predict OA progression status at 3 years in models accounting for age, gender, BMI, bone mineral content (BMC), knee pain, baseline knee status, and knee alignment, and adjusted using generalized estimating equations for the correlation between knees. All fractal signature terms (horizontal and vertical, linear and quadratic) were acquired from the medial subchondral region. These fractal signatures of the medial subchondral bone on baseline x-rays were significantly correlated with OA progression of the medial compartment based on JSN. The baseline fractal signatures of the medial subchondral bone were not associated with OA progression based on osteophyte, or with OA progression of the lateral knee compartment. In addition, age was independently predictive of medial and lateral JSN while knee alignment was independently predictive of medial JSN. Accounting for these other factors, BMI was only independently predictive of lateral osteophyte progression.

The predictors for OA progression can be used in a variety of ways. As noted above, the predictors can be used to identify rapid progressors as participants in an OA treatment trial to thereby decrease the number of trial participants needed to show an effect, which in turn, reduces costs and drug exposure. The predictors can also be used to predict incidence of OA (i.e., predict subsequent appearance of OA in a control or non-OA patient or subject; for instance after a knee injury to predict possibility of subsequent OA that would dictate need for more aggressive therapy). The predictors can also be used to monitor OA progression over time, to monitor efficacy of a therapeutic intervention or in a determination of what type of treatment should be given (e.g., drug type and dosing). The predictors can also be used to choose OA patients most in need of therapy on basis of high likelihood of progression.

EXAMPLE STUDY #1

Patients

This example involved a total of 159 participants (118 female, 41 male) who met the American College of Rheumatology criteria for symptomatic OA of at least one knee. In addition, all participants met radiographic criteria for OA with a Kellgren-Lawrence (KL) score of 1-3 in at least one knee. Exclusion criteria included the following: bilateral knee KL4 scores; exposure to a corticosteroid (either parenteral or oral) within 3 months prior to the study evaluation; knee arthroscopic surgery within 6 months prior to the study evaluation; known history of avascular necrosis, inflammatory arthritis, Paget's disease, joint infection, periarticular fracture, neuropathic arthropathy, reactive arthritis, or gout involving the knee, and current anticoagulation. A total of 186 participants were screened to identify the final 159 participants with radiographic and symptomatic knee OA of at least one knee. These analyses focused on the 138 participants (87%) who returned for follow-up evaluation 3 years later. Of the total 276 knees available for analysis, 10 were replaced at baseline and 18 replaced during the period of longitudinal follow-up leaving a total of 248 knees available for the final analyses. Age, gender, and measured body mass index (BMI, kg/m2) were collected as covariates. Knee symptoms were ascertained by the NHANES I criterion of pain, aching or stiffness on most days of any one month in the last year; for subjects answering yes, symptoms were quantified as mild, moderate, or severe yielding a total score of 0-4 for each knee.

Posteroanterior fixed-flexion knee radiographs were obtained with the SynaFlexer™ lower limb positioning frame (Synarc, San Francisco) with a ten degree caudal x-ray beam angle. X-rays were scored for KL grade (0-4), and individual OA radiographic features of joint space narrowing (JSN) and osteophyte (OST) were scored 0-3 using the OARSI standardized atlas for the medial and lateral tibiofemoral compartments. This resulted in total JSN scores of 0-6 and OST scores of 0-12 as all four margins of the knee joint were scored for this feature. Blinded rescoring of 78 knee radiographs was performed to calculate the intrarater reliability of the x-ray readings by weighted kappa statistic, which were as follows: for JSN kappa 0.71 (95% CIs 0.63-0.79); for OST kappa 0.73 (95% CIs 0.67-0.79).

For purposes of statistical modeling, knee OA baseline status was defined as the JSN score at baseline. Knee OA progression status was calculated as the change in JSN scores or the change in OST score for the tibiofemoral compartment over 3 years derived from baseline and follow-up x-rays read in tandem by two trained readers blinded to the clinical and bone texture data, but not blinded to the time sequence. Of the 248 knees available for analysis, 13% were defined as progressors on the basis of increase in joint space narrowing (JSN) over 3 years, and 69% on the basis of increase in osteophyte (OST). The progressor knees in this study were: 18 based on medial JSN, 14 based on lateral JSN, 75 based on medial OST, and 97 based on lateral OST. It was possible to have a change in OST in the absence of JSN change, however, except for one case, all progressors based on JSN also had increasing OST scores. Trabecular bone mineral density (BMD) and bone mineral content (BMC) were measured at the calcaneus of the dominant leg using a Norland Apollo™ DEXA. Knee alignment was measured manually to within 0.5 degrees on a weight-bearing "long-limb" (pelvis to ankle) anteroposterior radiograph as previously reported using the center at the base of the tibial spines as the vertex of the angle.

All X-rays were analyzed using the KneeAnalyzer™ application developed by Optasia Medical, Inc. The KneeAnalyzer utilizes computer aided detection based on statistical shape modeling to provide highly reproducible quantitative measurements of the medial compartment of the knee yielding separate vertical and horizontal fractal dimensions over a range of scales related to trabecular dimensions and referred to as signatures. All films were digitized using a VIDAR Diagnostic Pro Plus digitizer at 150 dpi (dots per inch), which converts to a pixel resolution of 169.3 microns.

Per the KneeAnalyzer requirements, all films were converted to uncompressed, 8-bit grayscale TIFF format from DICOM using the PixelMed Java DICOM Toolkit (an open source software package distributed by PixelMed Publishing). All analyses were performed with the fibula on the left-hand side of the image as viewed by the rater (images were flipped horizontally as necessary). Correction for magnification was achieved by analyst-assisted detection of the vertical column of beads in the SynaFlexer platform by the KneeAnalyzer. Joint segmentation was based on six manually selected initialization points at the lateral femur, medial femur, lateral tibia, medial tibia, lateral tibial spine, and medial tibial spine, which are indicated by the x's in FIG. 8A.

Once the initialization points were selected, the software determined the joint space boundary profiles for both the lateral and medial compartments and automatically identified the rectangular region 802 for fractal signature analysis in the medial subchondral bone based on the medial tibial joint profile. The FSA region of interest (ROI) 802 in FIG. 8B spanned three-quarters (¾) of the tibial compartment width, had a height of 6 mm (determined using SynaFlexer calibration), and left boundary aligned with the tip of the medial tibial spine. This ROI was standardized based on later work by Buckland-Wright who used this to avoid the periarticular osteopenia adjacent to marginal osteophytes. From this region, FSA was determined at a range of scales (termed radii) as determined by the software based on the pixel resolution and SynaFlexer calibration. The radii for FSA ranged in dimension from 3 pixels wide (0.4 mm) to the width of one-half (½) the height of the ROI (3 mm). The fractal dimensions in two directions were measured with rod-shaped structuring elements using a "box" counting approach. The FSA data provided by the software are referenced to the 'vertical filter'(horizontal fractal dimension) and the 'horizontal filter' (vertical fractal dimension). To avoid confusion, the data is described herein in terms of the horizontal fractal dimension (tension) and vertical fractal dimension (compression) and not according to the 'filter'.

A subset of six radiographs (3 OA, 3 non-OA) were analyzed by three analysts to test the impact of analyst on FSA. Two criteria were evaluated, the range and distribution of "filter" elements and the fractal signature for both the horizontal and vertical fractal dimensions.

The fractal signature (FS) data generated by the KneeAnalyzer application are 3-dimensional, where compression and tension fractal dimensions (FD) are measured over a range of radii for each knee X-ray, representing increasing lengths based on the pixel dimension. The FD measures are highly correlated along radius. The trends of compression and tension change were modeled over radius with second order (quadratic) multiple regression models using a non-centered polynomial, so that the multi-dimensional correlations between FD measures and radii were summarized by 2 polynomial "shape" parameters. Using the shape approach, precise alignment of radii across patients was not necessary, and the full use of the all the data could be made, thereby increasing the power to discern a potential difference between groups.

Clinical covariates, including age, gender, BMI, knee pain, bone mineral content (BMC), left versus right knee, knee alignment and baseline knee OA severity (categorical joint space narrowing 0-3), were included in the same statistical model with an analysis of co-variances (ANCOVA) framework and repeated measures. Linear mixed models and generalized linear models were used to adjust for correlations between knees.

To determine if the fractal signature variation was associated with any clinical factors, testing was performed as to whether the shapes of the polynomial curves were different among different groups of individuals, e.g., progressors vs. non-progressors. This was to test the interaction terms between the shape parameters and the group indicators. An investigation was performed as to whether the FD variations were associated with other clinical factors such as age, gender, BMI, and other covariates, adjusting for the shape of curves considered in the model.

The full statistical model was:

$$Y_{ijk} = u + a + g + BMI + BMC + KA + JSN + LR + r_k + r_k^2 + gID_i + r_k \times gID_i + r_k^2 \times gID_i + P_{ij} + e_{ijk};$$

where: $Y_{ijk}$ is the fractal dimension readings calculated at i-th status (progressor vs. non-progressor), j-th individual (left vs. right) and k-th radius; u is the grand mean; a is age; g is gender; KA is Knee Alignment; JSN is the Joint Space Narrowing at Baseline; LR is the left or right knee indicator; r is radius—linear term; $r^2$ radius—quadratic term; $gID_i$ is the group ID (e.g., i=0 if non-progressor; =1 if progressor); r*gID and r2*gID are the interaction terms; $P_{ij}$ is the random effect associated with the jth subject in group i; $e_{ijk}$ is the random error term, associated with the jth subject in group i at radius k.

Because it is observed that, in general, the correlations among FD measures are larger for nearby radii than far-apart radii, an auto-regressive correlation model of order 1 (i.e., AR(1) in SAS/mixed/repeated measures) was used. More sophisticated statistical models were investigated as well, e.g., with various interaction terms between/among fixed effects, and multiple intra-subject random correlation patterns. Eventually this model was selected because of its parsimony and efficiency.

To confirm in that the shapes of the polynomial curves could be used to predict disease progression, the estimates of the shape parameters of the polynomial curves from both the compression and tension fractal dimensions were included, together with other covariates, in a generalized linear model (GLM/GEE) to predict disease progression status. GLM/GEE was used to adjust for correlations within an individual because there were two curves from most individuals (left and right knees), and the shape parameters estimated from those curves are likely to be correlated. The linear predictors from the GEE model were used to predict scores for every knee.

The Receiver Operating Characteristic (ROC) curves were generated based on the prediction scores using 5-fold cross-validations. In the cross-validation, the data were divided randomly into 5 groups (or folds), 4 groups were used as training data for model building and the remaining 1 group was used for model validation. The false positive rate and false negative rate were calculated by averaging results from all 5 possible training-data/validation data combinations. A total of 300 cross-validations were performed and the averaged results were reported. Various statistical models containing different combinations of predicting variables were investigated. Data for the numbers needed to screen to predict one progressor were derived from the ROC curves for a range of false positive or type I error rates.

The full GLM/GEE model was:

$$Y_{ij} = u + a + g + BMI + BMC + KA + JSN + LR_j + HL + HQ + VL + VQ + P_i + e_{ij};$$

Where: $Y_{ij}$ is the disease progression status, defined as at least one grade change in joint space narrowing or at least one grade change in osteophyte. It is recorded at i-th individual, j-th knee (left vs. right); a is age; g is gender; KA is Knee Alignment; JSN is the Joint Space Narrowing at Baseline; HL is the linear shape parameter estimated from horizontal filter data; VL is the linear shape parameter estimated from Vertical filter data; HQ is the quadratic shape parameter estimated from horizontal filter data; VQ is the quadratic shape parameter estimated from vertical filter data; P is the patient ID (this factor is treated as a random effect in the model); and $e_{ij}$ is the random error term, associated with ith subject and jth knee.

A difference of 0.036 (std=0.03) was detected in the 2nd-order polynomial measure between the medial knee progressors and non-progressors. The power was high (0.996, at a type I error rate controlled at 0.05 with a two sided t test) for detecting a difference in this cohort given the 18 medial knee OA progressors and the 120 non-progressors.

The KneeAnalyzer software is semi-automated software requiring manual identification of six reference points in the knee image. Regarding the interrater reliability of fractal signatures, the impact of the analyst was small and non-significant. The filter elements and the fractal signatures were tested by linear regression of each analyst versus the mean filter element size or the mean fractal signature (horizontal and vertical) of the 6 knee radiographs. The fractal signatures (horizontal) gave intercepts and slopes (R2) for the three analysts of: 0.105+0.958 (0.93); −0.006+1.009 (0.86); and −0.99+1.032 (0.81). The fractal signatures (vertical) gave intercepts and slopes (R2) for the three analysts of: −0.05+1.022 (0.97); −0.13+0.94 (0.97); and −0.07+1.31 (0.97). The filter elements (to three decimal places) gave intercepts of 0 and slopes of 1.002, 1.002 and 0.995 respectively, with R2>0.99.

Since the analyst does not manually 'place' the box for fractal analysis, the 'magnification factor' from the Synaflexer™ calibration was reviewed, as well as the digital location of the box for the three analysts as a possible source for the small (and non-significant) variations. In all cases but one, the magnification factors were identical. In the exception there was a 2.8% variation between analyst 3 and the other two analysts. The median 'box' size for the group of patients was 157 (range 140-183) by 39 pixels (range 37-47). The differences in the box area were ≤9% for all analysts and all patients.

The impact of digitization was small. Comparison of trabecular integrity in digital and digitized films revealed that the acquired data spanned the same range of radii representing trabecular widths (0.3-3.0 mm), with the exception of the very smallest dimension (~2 smallest radius), which was not captured on the digitized films. However, the shape of the fractal signature curves was not impacted by digitization. Mapping digitized to native with interpolation gave the following regression: Digitized=1.019 Native−0.029 (R2=0.998). Based on these results, the use of digitally acquired images is likely to provide bone texture data on the smallest radii comparable to the previous analyses of macro-radiographs (e.g., 0.6-1.14 mm), but will span a broader range of larger radii (e.g., 0.06-3.0 mm).

The curves generated from all knees are shown in FIGS. 3A and 3B. Upon analysis of the total fractal data without global shape analysis, there was no discernible statistically significant association between fractal dimensions and progression status (for horizontal fractal dimension: p=0.42 for OST progression, and p=0.07 for JSN progression; for vertical fractal dimension: p=0.67 for OST progression, and p=0.15 for JSN progression). These results demonstrated the value, exemplified by analyses in past studies, of analyzing across groups within specific ranges of radii or trabecular size in order to draw any meaningful conclusions. In the past, this was typically done by subtraction of baseline from follow-up FSA data followed by group comparisons of data within specific ranges of trabecular widths.

However, the analyses of the systems and methods described herein modeled the overall shape of the curve of the fractal dimension versus radius. Two components of the shape curve were evident, a linear and a quadratic shape. This method avoided the problem of alignment of radii across individuals. FIGS. 5A and 5B shows the mean overall fractal signature shape curves of knee OA progressors and non-progressors. This method revealed decreased horizontal fractal dimensions (tension) and increased vertical fractal dimensions (compression) in progressors compared with non-progessors at particular regions of the curve.

The remaining analyses were conducted with linear and quadratic fitted fractal signature data. Bivariate associations with fractal signatures are shown in FIG. 9. The linear shape (radius) and the quadratic shape (radius$^2$) terms were significantly associated with fractal dimensions. The interaction of the shape terms and OA progression was strongly associated with horizontal fractal dimension. Calcaneal bone mineral density (BMD) and bone mineral content (BMC) were both associated with horizontal fractal dimension; the association with BMC was strongest so it was retained in lieu of BMD for subsequent analyses. Significant associations with vertical fractal dimensions included both the linear, and quadratic shape terms, as well as gender, age and body mass index.

The prognostic capability of baseline fractal signatures to predict OA progression status at 3 years was evaluated in models accounting for age, gender, BMI, BMC, knee pain, baseline knee status, and knee alignment, and adjusted using generalized estimating equations for the correlation between knees. See FIG. 10. All fractal signature terms (horizontal and vertical, linear and quadratic) were acquired from the medial subchondral region. Fractal signatures of the medial subchondral bone from baseline x-rays were significantly correlated with 3-year OA progression based on JSN of the medial compartment. The baseline fractal signatures of the medial subchondral bone were not associated with OA progression based on OST, or with OA progression of the lateral knee compartment. In addition, age was independently predictive of medial and lateral JSN, while knee alignment was independently predictive of medial JSN. Accounting for these other factors, BMI was only independently predictive of lateral osteophyte progression.

Figure 6:
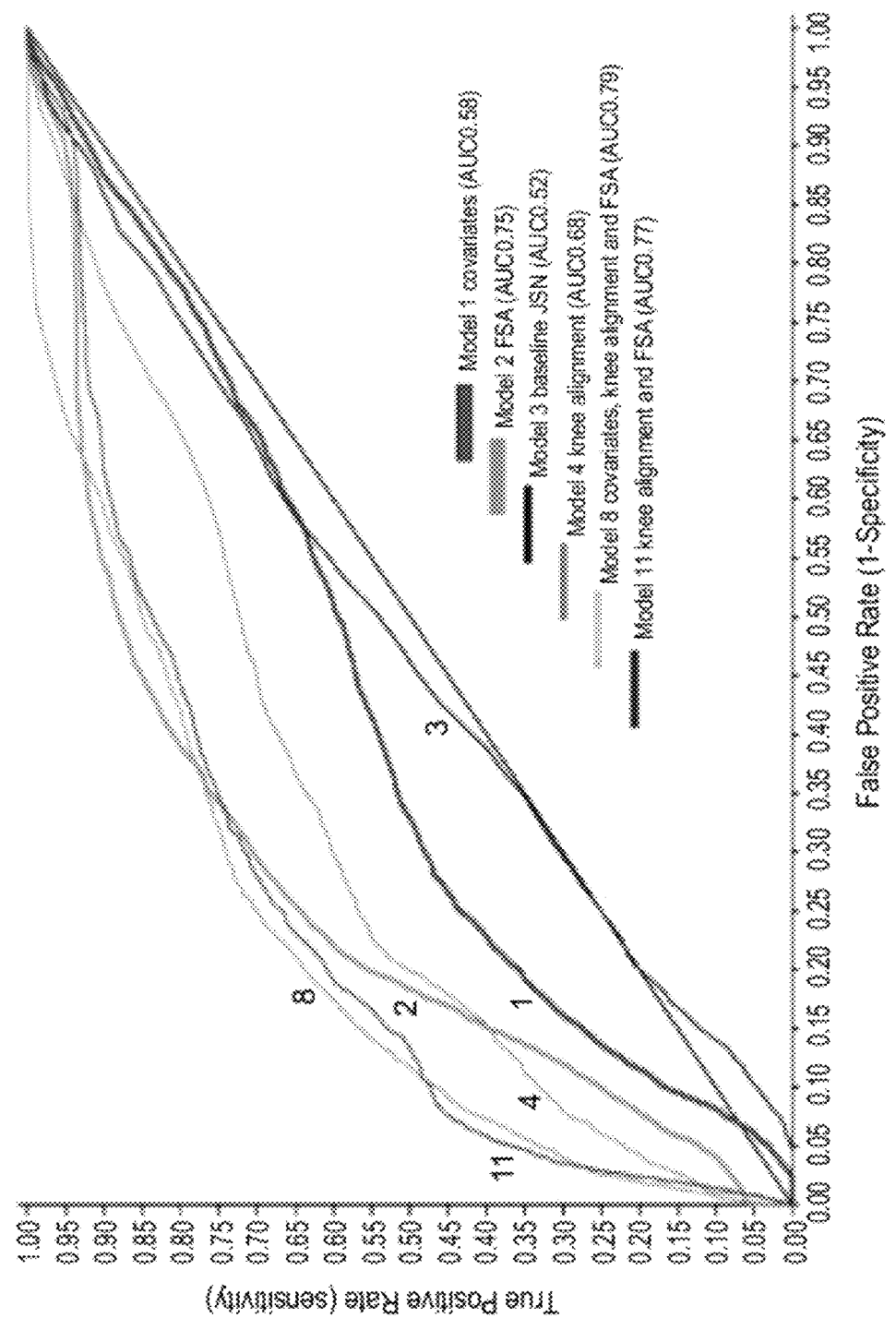
FIG. 6 shows Receiver Operating Characteristic curves (ROC) used to quantify the predictive capability (a composite measure made up of sensitivity and specificity measures) for medial OA JSN progression by fractal signatures and other variables, singly and in combination.

Receiver Operating Characteristic curves (ROC) were used to quantify the accuracy of predicting medial OA JSN progression by fractal signatures and other variables, singly and in combination. See FIG. 6. ROC curves were constructed for predicting medial joint space narrowing using a 5 fold cross-validation approach. The null model is expected to have an area under the curve (AUC) of 0.5; four random variables gave AUC 0.50. The traditional covariates (age, gender, BMI) fared no better than the random variables for predicting OA progression with AUC 0.52 (not shown). The addition of BMC and knee pain increased the predictive power only slightly (AUC 0.58). Baseline OA status (categorical joint space narrowing variable) alone was no better than the random variables (AUC 0.52) for predicting knee OA progression. FSA had a remarkably good predictive capability for OA progression yielding an AUC 0.75 with no improvement on addition of the covariates age, gender, BMI, BMC and knee pain (AUC 0.74). Among the other variables, only knee alignment was moderately predictive of medial JSN progression (AUC 0.68). The best model with the fewest variables (AUC 0.79) was not much better than FSA alone, and used all variables (age, gender, BMI, BMC, knee pain, knee alignment and FSA) but not baseline OA status. Six representative ROC curves are depicted in FIG. 6.

To gain an appreciation of how FSA might benefit clinical trial design, data was extracted from the ROCs to estimate the number needed to screen to identify one medial compartment progressor by this method. The predictive ability of the traditional covariates (age, gender, BMI, knee pain) and bone mineral content was compared to that of medial compartment FSA. As demonstrated for a variety of false positive rates, fewer individuals need to be screened in order to predict one progressor using FSA compared with the other covariates. At a type I error or false positive rate of 5%, 8 individuals would need to be screened by FSA versus 24 using the other covariates, amounting to 1:3 ratio to identify one medial knee OA progressor comparing the two methods. See FIG. 7.

EXAMPLE STUDY #2

From a total of 180 females, age ≥40 years, 127 participants (60 with knee OA, and 67 without knee OA who served as a healthy reference population) were included in this study based on availability of x-rays for at least two of three time-points (baseline, 12 and 24 months), and sufficient x-ray resolution (see below) for bone texture analyses. Inclusion criteria for OA participants were frequent symptoms in the signal knee, mild to moderate radiographic OA in the medial compartment of this knee, a body mass index (BMI) of ≥30, and a medial tibiofemoral joint space width of >2 mm in a posteroanterior modified Lyon-Schuss view. Healthy participants served as a reference population and had to show a complete absence of knee symptoms, no evidence of radiographic knee OA (Kellgren Lawrence grade 0 or 1), and a BMI of ≤28. All knee OA participants displayed mild to moderate radiographic OA in the medial femoro-tibial compartment (Kellgren Lawrence grades 2 to 3). In patients with bilateral radiographic knee OA, the more symptomatic knee was selected to be the signal knee; the knee of the dominant leg was selected to be the signal knee in all non-knee OA participants. Participants with a history of intra-articular fracture, arthroplasty, meniscectomy, crystalline diseases, knee infection, and avascular necrosis were excluded. While anterior cruciate ligament (ACL) tears were not part of the exclusion criteria, a review of medical histories revealed no cases of ACL injury and/or reconstruction. Specifics on the medication that the participants were allowed to take during the study were described in Eckstein, 2008.

Posteroanterior modified Lyon Schuss knee radiographs were obtained with the SynaFlexer™ lower limb positioning frame (Synarc, San Francisco) with a variable caudal x-ray beam angle chosen by fluoroscopy to minimize the tibial intermargin distance. Films were acquired digitally. The mean (SD) resolution was 138 (33) microns/pixel for x-rays. In some cases, more than one knee x-ray was performed for an individual, each with a different x-ray beam angle to optimize (i.e. minimize) the intermargin distance (the vertical distance between the anterior and posterior tibial margins in the 2-D x-ray image). The images with the smallest intermargin distances were chosen for bone texture analysis. Overall, 381 images were available for analysis (129 (run1)+127 (run2)+ 125 (run3)).

All X-rays were analyzed using the KneeAnalyzer™ application. As discussed above, the KneeAnalyzer™ software utilizes computer aided detection based on statistical contour modeling to provide highly reproducible quantitative measurements of the medial compartment of the knee. The bone texture analysis was performed as described above in the discussion of Study #1. In addition, the software tool provided automated measurements of the medial minimum joint space width (mm) and medial cartilage area (mm$^2$). Cartilage area represents the joint space width integrated over the majority of the medial compartment. The inner and outer cartilage area boundaries (automated calculation) were defined by the position of the inner and outer margins of the tibial fossa landmark respectively, as determined by the model-fitting process. These two points were defined as follows: inner margin of tibial fossa was the point where the lower margin of the tibial fossa (bowl) converged with the projected edge of the tibial plateau, on the side nearest to the inner edge of the knee; the outer margin of tibial fossa was the point where the lower margin of the tibial fossa converged with the projected edge of the tibial plateau, on the side nearest to the outer edge of the knee. The two points were located implicitly by the model-based segmentation algorithm for finding the whole tibial plateau; they are anatomical landmarks which have been marked consistently in a training set of example images, and the statistical model learns how to locate them. Although the KneeAnalyzer tool allows the user to edit the positions of the inner and outer cartilage area boundaries, this was assiduously avoided to insure reproducibility.

Analyses were performed separately in the OA and reference population subsets. The bone texture by radius trends in the vertical and horizontal dimension were modeled with second order (quadratic) multiple regression models using a non-centered polynomial, so that the multi-dimensional correlations between fractal dimension measures and radii were summarized by 2 polynomial "shape" parameters. Age and baseline knee OA severity (joint space width or cartilage area) were included in the same statistical model with an analysis of co-variances (ANCOVA) framework and repeated measures.

To determine if the bone texture variation was associated with any clinical factors, an evaluation was made of the association of the shapes of the polynomial curves and knee OA progression, and knee OA severity. Two definitions of knee OA progression were tested: change in medial minimum joint space width, and change in cartilage area. The same two outcome variables were evaluated in cross-section to assess the association of bone texture and knee OA severity. The full statistical model was described above in the discussion of study #1.

A total of 60 knee OA and 67 age-matched non-knee OA participants had available knee x-rays from baseline, and 12- and 24-month follow-up. The OA participants had a mean (SD) age of 58±8.5 years, and a mean (SD) BMI of 35.6±5.5. The 67 non-knee OA participants had a mean (SD) age of 55±9.0 years, and a mean (SD) BMI of 23.2±2.4 kg/m2.

To validate bone texture as a biomarker of OA progression, progression was defined as the difference of the computer-measured parameters (cartilage area and minimum joint space width) between the baseline and follow-up times (12 and 24 months). Both the linear (radius_OAprogression) and quadratic (radius$^2$_OAprogression) terms were assessed in the model. In the OA participants, the mean (SD) change in cartilage area and joint space width were −3.23 (9.49) millimeters and −0.22 (0.71) millimeters respectively. Baseline subchondral medial bone texture predicted OA progression in the knee OA participants. See FIG. 11.

Specifically, bone texture in the vertical (compression) dimension predicted change in cartilage area at 12 and 24 months (FIG. 11). The association was stronger for the 24-month prediction. Bone texture in the vertical (compression) dimension also predicted change in joint space width but only over 24 months (FIG. 11). The horizontal dimension of bone texture was not associated with either outcome. Most interestingly, subchondral bone texture was a more robust predictor of change in cartilage area than change in joint space width.

In the reference population, the mean (SD) change in cartilage area and joint space width were −0.62 (6.84) millimeters and 0.03 (0.33) millimeters respectively. Baseline subchondral medial bone texture was not associated with change in either cartilage area or change in joint space width in this age-matched non-OA reference population, demonstrating that the changes observed in the OA population were not due to aging, but specific for the disease process.

Figure 12:
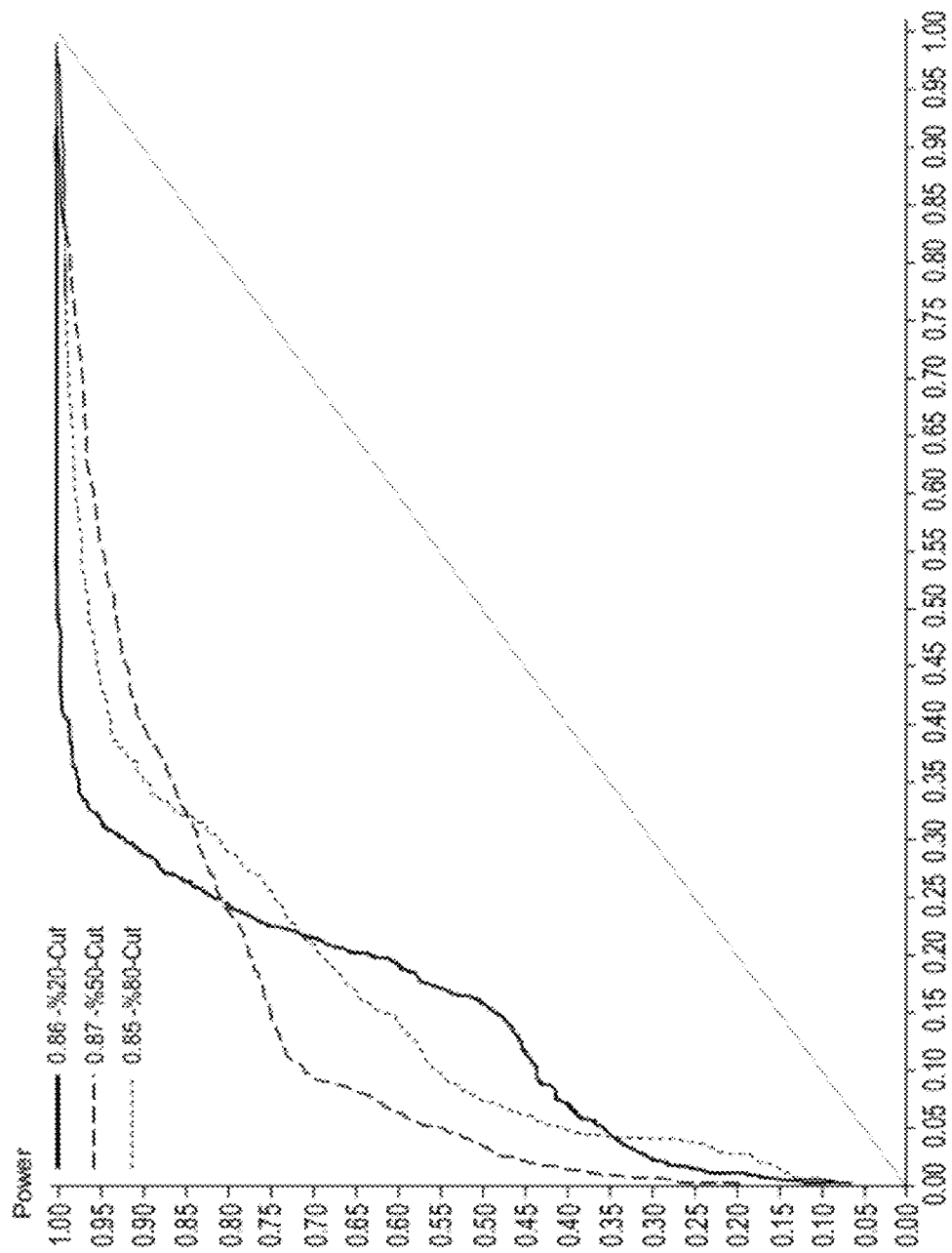
FIG. 12 shows further example ROC curves.

To better understand how bone texture might benefit clinical trial design, ROC analyses in the knee OA cohort were performed. With ROC curves the ability of bone texture to predict change in cartilage area and change in joint space width was evaluated. Because change in cartilage area was a continuous measure, it was split into binary groups with various percentile cut-off points including the $90^{th}$, $75^{th}$, $50^{th}$, $25^{th}$ and $10^{th}$ percentiles to generate a family of ROC curves. Representative curves using the $80^{th}$, $50^{th}$ and $20^{th}$ percentile cut-off points are shown in FIG. 12. The ROCs demonstrated maximal 70-80% capacity (area under the curves) of bone texture for predicting change in cartilage area from baseline to 24 months.

Although this study was smaller (60 versus 138 OA participants) and of shorter duration (maximal 2 instead of three years) than Study #1, this study validated bone texture as a prognostic biomarker for knee OA progression. Taken together with study #1, this shows that bone texture can predict progression ensuing over a 12-36 month timespan, which happens to be the timespan of a typical OA clinical trial. Thus, this technique can be used, example, to identify knee OA participants for trial purposes who could be expected to progress within the duration of the trial. The significant associations seen in study #2 were only for the vertical (compression) bone texture direction and study #1 demonstrated associations with OA progression and both the horizontal (tension) and vertical dimensions of bone texture. The association was stronger for 24-month prediction, likely because it provided adequate time for measurable change in the joint parameters of cartilage area and joint space narrowing. Furthermore, subchondral medial bone texture is an OA severity marker and could perhaps be considered an alternative outcome measure for clinical trials.

As expected, there was no significant change in cartilage area or joint space width over time in the reference population. This age-matched population, followed for the same time period as the knee OA participants, showed no association of bone texture and change in either cartilage area or joint space width demonstrating that the changes in these parameters are specific to the OA disease process rather than ageing.

A strength of study #2 was the high quality of the digital x-rays, providing radiographic outcomes of progression as robust as is currently possible. This enabled comparing of bone texture and the traditional OA trial outcome, joint space narrowing. Manual selection of points in the joint profiles was minimized and found unnecessary, therefore, similar results should be readily obtained by others using the commercially available KneeAnalyzer software. Bone texture may be a valuable adjunct in OA clinical trials for identifying progressors, thus providing a means of enriching a trial with progressors at entry and thereby increasing power and/or reducing costs due to the need for fewer trial participants.

In addition to use as a prognostic indicator, bone texture may also serve as a surrogate for minimum joint space width, the current knee OA clinical trial outcome. The potential advantage of bone texture over joint space width as an outcome variable for OA clinical trials is that bone texture is robust to varying radiographic exposure, to changing pixel size, and to knee repositioning.

To evaluate the surrogacy of bone texture for minimum joint space width, optimized knee x-rays were necessary to assure the validity of the joint space width measurements. To date, three prior studies have longitudinally evaluated tibial cancellous bone texture changes of the knee OA but results have been conflicting with two positive studies and one negative study. The results of the systems and methods described herein are positive, showing that bone texture correlates with change in joint space width and change in cartilage area (FIG. 13). These results also show that bone texture correlates even more strongly with 'cartilage area' on an x-ray; cartilage area can be thought of as the joint space width area integrated over the area of the joint space of the knee medial compartment. Therefore, these bone texture analyses provide a new measure for OA clinical trials.

While the systems and methods have been described in connection with what is presently considered to practical and preferred embodiments, it is to be understood that these systems and methods are not limited to the disclosed embodiments. For example, the systems and methods can be applied to predicting lateral compartment progression using lateral compartment bone texture and to joints other than knees.

We claim:

1. A method of generating a predictor of osteoarthritis (OA) progression of a joint, the method comprising:
    generating fractal dimension curves for horizontal and vertical trabecular components associated with a region of interest of an image of the joint;
    performing a shape analysis to model a shape of each of the fractal dimension curves;
    estimating a plurality of shape parameters from the modeled shape of each of the fractal dimension curves; and
    applying a statistical model to the plurality of shape parameters to calculate a predictor of OA progression.

2. The method according to claim 1, wherein the image comprises an x-ray.

3. The method according to claim 1, wherein the image comprises an MRI image.

4. The method according to claim 1, wherein the image comprises a computed tomographic image.

5. The method according to claim 1, wherein the shape analysis comprises a polynomial regression.

6. The method according to claim 1, wherein the shape analysis comprises a second order polynomial regression.

7. The method according to claim 1, wherein the joint is a knee.

8. The method according to claim 1, wherein the statistical model comprises a statistical generalized estimating equation (GEE) model.

9. The method according to claim 1, wherein the statistical model comprises a statistical linear mixed model.

10. An apparatus comprising:
    a processor;
    a memory coupled to the processor, the memory having instructions stored therein,
    wherein the processor executes instructions from the memory to generate a predictor of osteoarthritis (OA) progression of a joint by performing operations comprising:
        generating fractal dimension curves for horizontal and vertical trabecular components associated with a region of interest of an image of the joint;
        performing a shape analysis to model a shape of each of the fractal dimension curves;
        estimating a plurality of shape parameters from the modeled shape of each of the fractal dimension curves; and
        applying a statistical model to the plurality of shape parameters to calculate a predictor of OA progression.

11. The apparatus according to claim 10, wherein the shape analysis comprises a polynomial regression.

12. The apparatus according to claim 10, wherein the joint is a knee.

13. A non-transitory computer readable medium storing program code which, when executed, causes a computer to perform steps comprising:
    generating fractal dimension curves for horizontal and vertical trabecular components associated with a region of interest of an image of a joint;
    performing a shape analysis to model a shape of each of the fractal dimension curves;
    estimating a plurality of shape parameters from the modeled shape of each of the fractal dimension curves; and
    applying a statistical model to the plurality of shape parameters to calculate a predictor of OA progression.

14. The computer readable medium according to claim 13, wherein the shape analysis comprises a polynomial regression.

15. The computer readable medium according to claim 13, wherein the joint is a knee.

16. A system comprising processing circuitry and the non-transitory computer-readable medium according to claim 13.

17. A method comprising:
    generating fractal dimension curves for horizontal and vertical trabecular components associated with a region of interest of joint images for osteoarthritis patients;
    performing a shape analysis to model a shape of each of the fractal dimension curves;
    estimating a plurality of shape parameters from the modeled shape of each of the fractal dimension curves;
    applying a statistical model to the plurality of shape parameters to calculate a predictor of OA progression for each patient; and
    based on the predictors, identifying patients at high risk of progression from among the patients.

18. A method comprising:
    generating fractal dimension curves for horizontal and vertical trabecular components associated with a region of interest of joint images for multiple clinical trial candidates;
    performing a shape analysis to model a shape of each of the fractal dimension curves for each of the trial candidates;
    estimating a plurality of shape parameters from the modeled shape of each of the fractal dimension curves for each of the trial candidates;
    applying a statistical model to the plurality of shape parameters for each candidate to calculate a predictor of OA progression for each candidate; and
    based on the predictors, identifying clinical trial participants from among the clinical trial candidates.

19. A system comprising:
    memory storing instructions for generating a predictor of osteoarthritis (OA) progression of a joint;
    a processing system, including at least one processor, in communication with the memory, the processing system executing the instructions to generate the predictor by performing operations comprising:
        generating fractal dimension curves for horizontal and vertical trabecular components associated with a region of interest of an image of the joint;

performing a shape analysis to model a shape of each of the fractal dimension curves;
estimating a plurality of shape parameters from the modeled shape of each of the fractal dimension curves;
applying a statistical model to the plurality of shape parameters to calculate a predictor of OA progression.

20. The system according to claim 19, wherein the image comprises an x-ray.

21. The system according to claim 19, wherein the shape analysis comprises a polynomial regression.

22. The system according to claim 19, wherein the shape analysis comprises a second order polynomial regression.

* * * * *